United States Patent
Ross et al.

(10) Patent No.: US 6,822,226 B2
(45) Date of Patent: Nov. 23, 2004

(54) CORONA IONIZATION SOURCE

(75) Inventors: Stuart Keith Ross, Salisbury (GB);
Andrew John Bell, Salisbury (GB)

(73) Assignee: The Secretary of State for Defence in Her Britannic Majesty's Government of the United Kingdom of Great Britain and Northern Ireland (GB)

( * ) Notice: Subject to any disclaimer, the term of this patent is extended or adjusted under 35 U.S.C. 154(b) by 0 days.

(21) Appl. No.: 10/471,952

(22) PCT Filed: Mar. 21, 2002

(86) PCT No.: PCT/GB02/01357

§ 371 (c)(1),
(2), (4) Date: Sep. 16, 2003

(87) PCT Pub. No.: WO02/078047

PCT Pub. Date: Oct. 3, 2002

(65) Prior Publication Data

US 2004/0079879 A1 Apr. 29, 2004

(30) Foreign Application Priority Data

Mar. 23, 2001 (GB) .............................. 0107311

(51) Int. Cl.$^7$ ................................. H01J 49/00
(52) U.S. Cl. ....................... 250/287; 250/286; 250/288
(58) Field of Search ................ 250/287, 286, 250/288

(56) References Cited

U.S. PATENT DOCUMENTS

| | | | |
|---|---|---|---|
| 4,445,038 A | | 4/1984 | Spangler et al. |
| 5,234,838 A | | 8/1993 | Bacon, Jr. |
| 5,283,199 A | | 2/1994 | Bacon, Jr. et al. |
| 5,574,277 A | * | 11/1996 | Taylor ........................ 250/281 |
| 6,225,623 B1 | * | 5/2001 | Turner et al. ............... 250/286 |

FOREIGN PATENT DOCUMENTS

| | | |
|---|---|---|
| GB | 1306534 | 2/1973 |
| GB | 1604926 | 12/1981 |
| GB | 2345378 | 7/2000 |

OTHER PUBLICATIONS

Losch et al., "Method and Apparatus for Ion Mobility Spectrometry", Pub. No.: U.S. 2003/0209665 A1, publication date: Nov. 13, 2003.*

* cited by examiner

Primary Examiner—John R. Lee
Assistant Examiner—Zia R. Hashmi
(74) Attorney, Agent, or Firm—Dean W. Russell; Kilpatrick Stockton LLP

(57) ABSTRACT

A corona discharge ionization source is disclosed in which neutral species are removed by directing a flow of oxygen containing gas in a direction substantially different to that of the ion flow. The ion profiles produced are similar in many respects to those produced by a $^{63}$Ni source, thus an alternative, non-radioactive, ion source is offered.

19 Claims, 6 Drawing Sheets

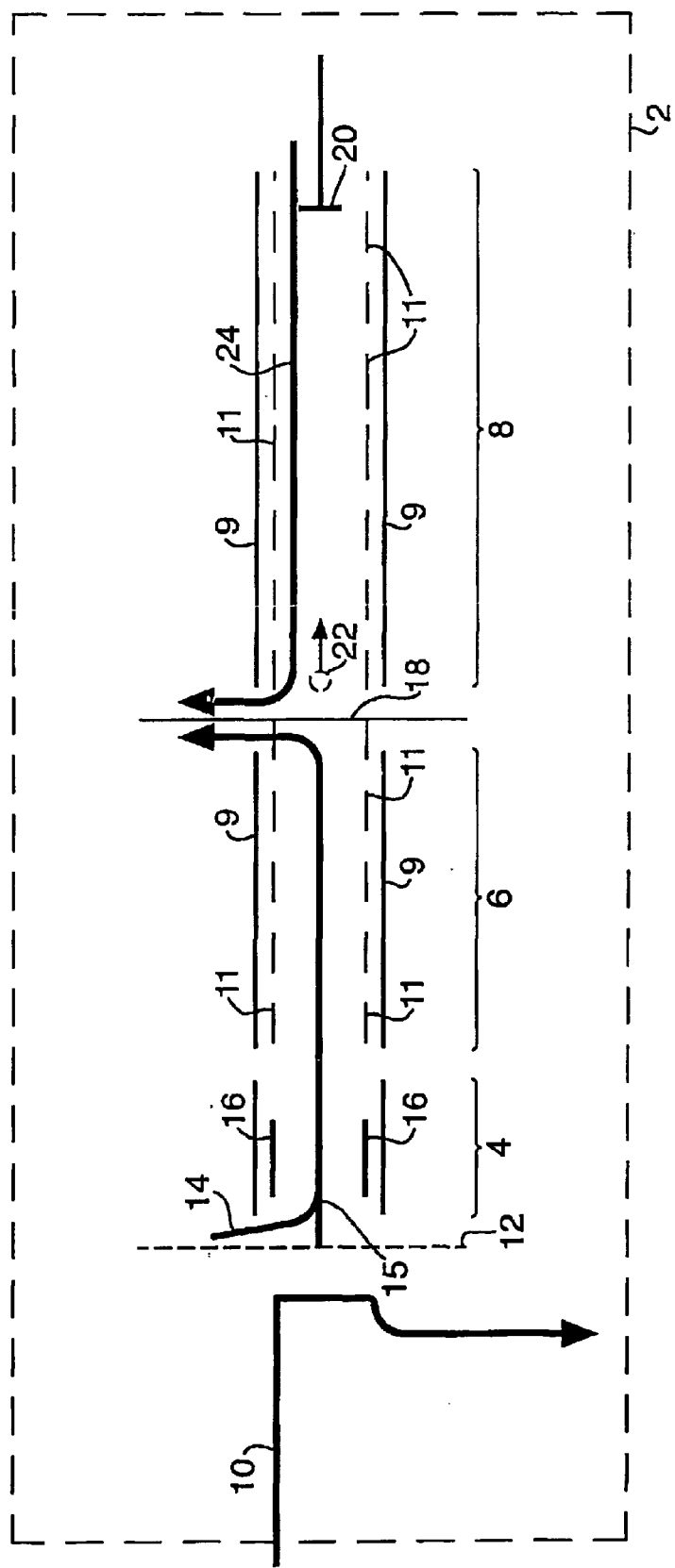

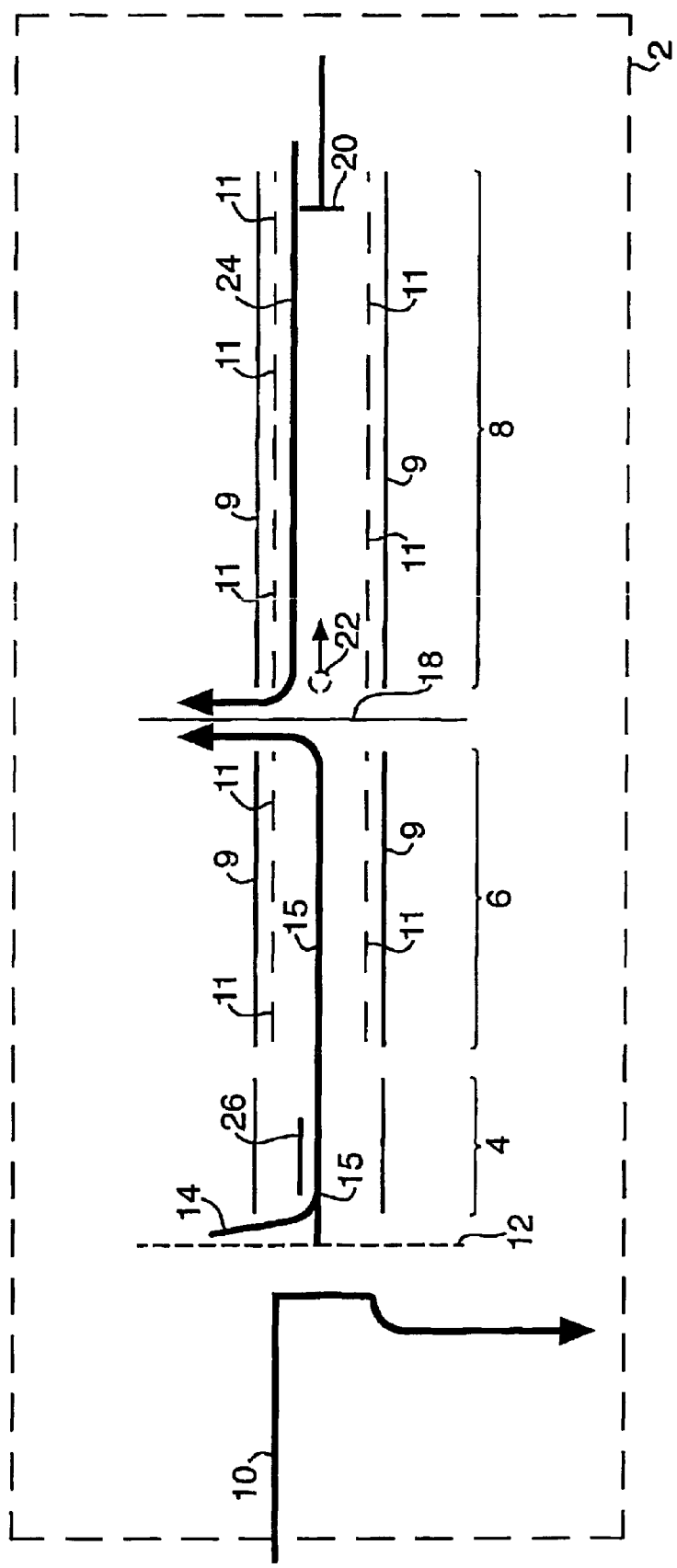

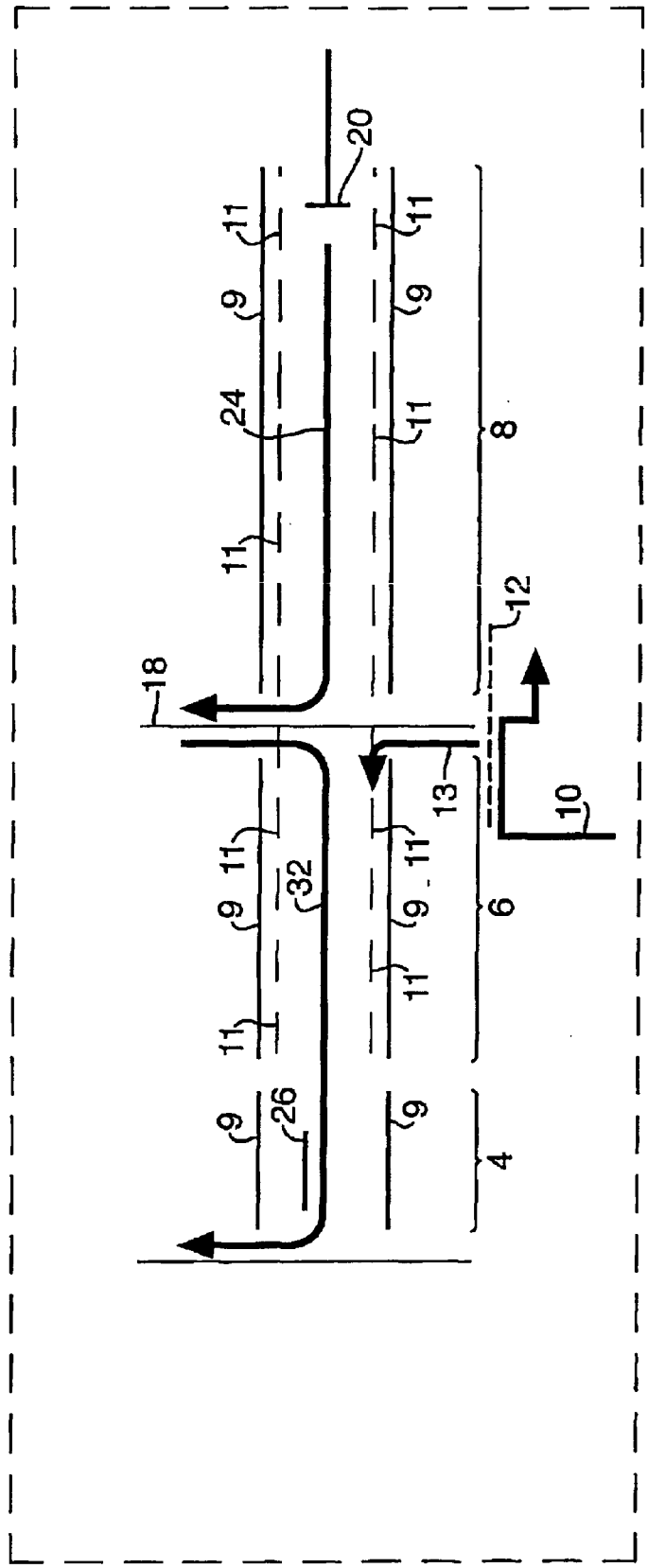

CORONA IONIZATION SOURCE

CROSS REFERENCE TO RELATED APPLICATIONS

This application is the U.S. national phase of International Application No. PCT/GB02/01357 filed on Mar. 21, 2002 published in English as International Publication No. WO 02/078047 A2 on Oct. 3, 2002, which claims priority to Great Britain Application No. 0107311.3 filed on Mar. 23, 2001, the contents of which are hereby incorporated by reference.

This invention relates to corona ionisation sources and in particular to continuous corona ionisation sources used in ion mobility spectrometry.

Ion mobility spectrometers are used in numerous applications such as the detection of narcotics, explosives and chemical warfare agents in air and for environmental monitoring.

A typical ion mobility spectrometer (IMS) such as that described in U.S. Pat. No. 4,777,363 comprises an ionisation source, a reaction region and a drift region. As monitoring/detection takes place at ambient atmospheric pressure, ionisation of the sample gas at atmospheric pressure is required. After ionisation, ions generated from the sample gas are expelled into a drift region where, under the influence of an electric field and collisions with a counter-flowing drift gas, the ions attain a constant velocity before arriving at a collector. The ion mobility spectrum obtained is characteristic of the sample being investigated.

Radioactive materials, such as $^{63}$Ni, are traditionally used as the ionisation sources in ion mobility spectrometers. The output from such radioactive sources is highly stable, and, in addition, they are noise and power free. However, radioactive sources have to be handled and disposed of with great care and the exposure of operating personnel to ionising radiation has to be carefully controlled and monitored. Taking all the necessary precautions in relation to the use, transportation, storage and disposal of devices incorporating radioactive sources can therefore prove costly.

Continuous corona ionisation sources have previously been used in IMS systems as an alternative to the use of radioactive sources. The ions produced by an IMS incorporating a continuous corona ionisation source and operating in negative mode (i.e. producing and collecting negatively charged ions) have however been found to differ markedly from the ions produced using a radioactive $^{63}$Ni ionisation source. See, for example, B Gravendee and F J de Hoog, J Phys B: At Mol Phys 20, 6337 (1987) for a discussion of the ionic species produced when air is ionised by a continuous corona ionisation source. The major problem is that neutral species formed during the ionisation process react with the initially formed reactant ion species. This results in the formation of unreactive ions which are significantly more stable to reaction than those produced by radioactive $^{63}$Ni ionisation sources, and which do not react so readily with sample vapour. Consequently, the sensitivity of IMS systems incorporating continuous corona ionisation sources can be low and it is commonly accepted by those skilled in the IMS field that continuous corona ionisation sources are unsuitable alternatives to traditional radioactive ionisation sources.

Various pulsed corona discharge sources have also been developed and, to a limited extent, these overcome some of the disadvantages associated with the use of continuous corona ionisation sources that are described above. However, pulsed corona discharge sources are expensive, involve complex pulsing, triggering and timing delays and have to be synchronised with gate opening events. As such there is still a need for improvements to the corona ionisation apparatus to improve ion mobility spectral data to make this a viable alternative to radioactive ionisation sources. Furthermore, there remains a need to develop a corona discharge ionisation apparatus, for use with an ion mobility spectrometer, whereby the unwanted side reaction between the neutral species and the reactant ion species, both formed during the initial ionisation stage, is minimised or eliminated. This would ensure that a more efficient reaction is achieved between the initially formed reactant ion species and the sample material, in turn improving the spectral results.

Various ion mobility spectrometers have been disclosed in the prior art. For example U.S. Pat. No. 4,445,038 discloses an apparatus for simultaneous detection of positive and negative ions in ion mobility spectrometry comprising dual drift regions respectively on either side of a centrally located reaction region; U.S. Pat. No. 5,234,838 discloses an ion mobility spectrometer for the analysis of ammonia whereby dimethly methyl phosphonate is added to the carrier gas stream prior to application of the carrier gas stream into the ionisation chamber thus forming clusters with the ammonia which have different drift times; and U.S. Pat. No. 5,283,199 discloses an ion mobility spectrometer for the analysis of chlorine dioxide whereby a controlled quantity of amine is added to the carrier gas stream prior to application of the carrier gas stream into the ionisation chamber thus suppressing the chlorine peak.

Although these documents optionally disclose the use of corona ionisation sources none of the documents specifically address the problem of improvement of the quality of corona ionised ion mobility spectra. More specifically they do not address the problem of how to minimise, or eliminate, the interaction of the neutral and reactant ion species in the ionised gas. Interestingly the apparatus of each of these documents has a configuration such that a certain flow of drift gas, whose primary role is to separate ions in the drift region, may pass from the drift region into the ionisation region of the spectrometer. However, this has the secondary effect of interfering with the flow of material in the ionisation region including sweeping neutral material to the exhaust. Such neutral material may include sample material introduced into the ionisation region and neutral species produced during the ionisation process.

Several problems are associated with configurations such as those described in the prior art. These include that the drift gas may not pass sufficiently closely to the ionisation source to efficiently remove the problematic neutral species formed in the ionisation gas; that the rate of flow of the drift gas into the ionisation region may be inconsistent as a result of having to pass through a shutter grid; that it is not possible to adjust the flow of any drift gas in the ionisation region separately from the flow rate in the drift region; and that the removal of neutral material will result in dilution of the sample material with a corresponding reduction in sensitivity.

Thus there remains the problem of how to efficiently remove the neutral species formed during the ionisation process from the ionised gas thus minimising or eliminating the interaction of the neutral and initially formed reactant ion species. There also remains the problem of how to maximise the efficiency of the reaction between the initially formed reactant ion species and the sample material. Finally there remains the problem of how to achieve this effect without affecting the use of the drift gas to separate ions in the drift region of the spectrometer. It is an object of this invention to mitigate some of the disadvantages, as described above, that are associated with the use of corona ionisation sources.

According to a first aspect the present invention relates to an apparatus for ionisation of a gas comprising a corona ionisation source, a means for flowing gas past the corona ionisation source, and a means for applying an electric field to move any ions produced by the corona ionisation source away from the corona ionisation source, characterised in that the direction of gas flow through the corona ionisation source is substantially different to the direction of the ions in the esectric field.

According to a second aspect, the present invention relates to an ion mobility spectrometer comprising an apparatus for ionisation of a gas as characterised in the first aspect of the invention.

Herein, the term "substantially different" shall be taken to mean a difference between the direction of electric field induced ion flow from the corona ionisation source and the direction of gas flow past the corona ionisation source, such that ions produced by the ionisation source become spatially separated from any neutral species produced by the ionisation source.

Herein the term "reactant ions" relates to the reactive ions which are initially formed when the gas is ionised by the corona discharge source. Ideally these ions later react with the sample material to form ionised sample species which then pass into the drift region and are separated prior to detection by the ion mobility spectrometer.

Herein the term "neutral species" relates to the neutral species which are initially formed when the gas is ionised by the corona discharge source.

Herein the term "unreactive ions" relates to the ions which form as a result of the side reaction which occurs between the reactant ion species and the neutral species. These unreactive ions are not able to further react with the sample material.

Directing the flow of ions and the flow of gas from the ionisation source in substantially different directions, and thus spatially separating ions and neutral species formed by the corona, prevents any further chemical reactions between the neutral species and the reactant ions from occurring. This provides ion mobility spectra substantially similar to those produced using radioactive ionisation sources, and mitigates some of the disadvantages of using corona ionisation sources in ion mobility spectrometers that are described above. Any inert gas would be useful in the present invention to be used to flow past the corona ionisation source in a substantially different direction to the flow of ions in the electric field. Optionally the inert gas may be dried before use to remove some or all of the water that may be present. It is preferred that the inert gas is air.

Advantageously, the corona ionisation source is a continuous corona ionisation source. Continuous corona ionisation sources have the advantage, compared to pulsed corona discharge ionisation sources, of being relatively inexpensive. Continuous corona ionisation sources are also free from the complex pulsing, triggering, delay timing and shutter synchronisation requirements of pulsed corona sources. Many different corona ionisation sources are available and the exact source to be used will vary depending on the source material, the corona energy and the inert gas to be ionised. One of ordinary skill in the art will be able to identify a suitable corona ionisation source for use in any given instance. The corona ionisation sources comprise a needle which can be made from a wide variety of metal materials. Commonly used examples include gold, platinum, steel, stainless steel and many metal alloys. The diameter of the corona needle will vary depending on the conditions, particularly the corona energy which is being applied. Examples of needle sizes include a 10 $\mu$m diameter, a 50 $\mu$m diameter, or a large atmospheric pressure chemical ionisation needle which has a diameter of 10,000 $\mu$m tapering down to a point. In order to supply the corona energy required for ionisation of the inert gas a current is applied to the needle. A wide range of currents can be used depending on the diameter of the needle and the inert gas to be ionised. Again one of ordinary skill in the art will be able to identify most suitable current required for the specific circumstances by routine experiment.

Conveniently, the flow of gas past the corona ionisation source may be continuous or alternatively the flow may be periodic. In other words, the gas may either flow continuously past the corona ionisation source or it may be periodically flushed past the corona ionisation source. It is preferred that if a continuous corona ionisation source is used that the flow of gas past the source in a direction substantially different to the direction of flow of the ions in the electric field is also continuous. A range of air flow rates can be used. Again the exact flow rate of the gas past the corona needle will vary from system to system depending on the corona needle size, the corona energy and the inert gas to be ionised and will therefore need to be optimised by one skilled in the art by routine experimentation. It is likely that the lower the corona energy the lower the flow rate that will be required. It is desirable that the flow rate of gas be adjustable such that it can be varied until the optimum rate is determined for the system in question. In an optimum operation the flow rate should be adjusted such that it is able to adequately flush neutral species from the ionised gas without affecting the flow of ionised species away from the corona needle in the electric field. This can be determined by routine experiment by one skilled in the art by optimising the sensitivity of the system to either maximise the concentration of initially formed reactant ions or by maximising the concentration of the sample product ion.

In order to minimise complexity of the ionisation chamber it is preferred that the inert gas to be ionised and the inert gas that flows past the corona ionisation source in a direction substantially different to the direction of flow of the ions in the electric field is the same gas. In this mode some of the inert gas will be ionised by the corona ionisation source as it flows past the source and other parts of the gas will be used to flush away any neutral species form in the ionised gas.

The sample material can be introduced either into the ionisation region such that the sample gas mixes with the ionised gas prior to the mixture passing into a reaction region or the sample material can be introduced directly into the reaction region. It is preferred that the flow rate of the gas past the ionisation source be adjusted such that it is able to flush neutral species from the ionised inert gas whilst flushing as little of the sample material from the ionisation region or reaction region as possible. One advantage of introducing the sample directly into the reaction region is that the flow of inert gas past the ionisation source can be isolated from the introduction of the sample material. This means that the sample material will not be diluted by a flow of gas and the reaction between the sample material and the ionised species will be concentrated thus improving its efficiency.

It is highly preferred that the apparatus also comprises a means for flowing gas through the drift region which is exhausted from either the reaction region or the drift region.

It is preferred that this exhaust point is arranged within the apparatus such that it does not interfere with the flow of either the sample material or any ionised material in the apparatus. Such an apparatus comprises at least two means for flowing gas—a first means which flows gas past the ionisation source and the second means which flows gas through the drift region. Furthermore, it is preferred that each of the means is independently adjustable such that the flow rate of each gas can be separately altered. This allows that the flow rate of the gas in the ionisation chamber can be optimised to efficiently flush out neutral species. Independently the flow rate of the gas through the drift region can be optimised to give good separation of the ionised sample material. It is likely that, in order to achieve optimal spectral results, that these two flow rates will be different. In order to maximise the benefit from such a design it is preferred that the apparatus has a drift gas inlet and a drift gas outlet in the drift region allowing for throughput of the drift gas. The apparatus should have a further flush inlet either in the ionisation region, or in the reaction region, with a flush outlet in the ionisation region to allow for throughput of the flush gas past the ionisation source in a direction substantially different to the direction of flow of the ions in the electric field. The flush outlet should be positioned in the ionisation region so as to achieve optimum flow of the gas past the ionisation source.

Although the drift region can comprise any drift tube, in an apparatus of the present invention it is preferred that the drift tube is a flexible modular system constructed of alternating rings of gold plated stainless steel and ceramic such as those that can be supplied by Graseby Ionics (Watford, UK). It is preferred that ions are gated into the drift region using a suitable gating device such as a Bradbury Neilsen shutter. The drift tube may be assembled to be any convenient length and again this will be determined by one skilled in the art on a case by case basis by routine experimentation and depending on the sensitivity and resolution required. Finally any suitable field strength can be applied to the drift tube and one of ordinary skill in the art will be able to identify a suitable field.

In a further embodiment the apparatus for ionisation of a gas comprises an ionisation region comprising a corona ionisation source, a reaction region and a drift region, wherein the means for flowing gas past the corona ionisation source has a flush inlet in the ionisation region and a flush outlet also in the ionisation region such that the direction of gas flow through the corona ionisation source is substantially different to the direction of flow of the ions in the electric field, and wherein the sample material is introduced into the reaction region. In this arrangement the neutral species produced by the corona source are flushed from the ionisation region whereas the reactant ions pass into the reaction region to react with the sample. This apparatus has several advantages. Firstly the same inert gas can readily be used as the ionisation gas and flush gas. Secondly the flow rate can be adjusted to maximise the flush rate of neutral species to minimised unwanted side reactions without having to be additionally concerned with inadvertently flushing away any unreacted sample material. Finally the neutral species are fully flushed before the reactant ions interact with the sample material such that there is a reduced possibility of side reactions which degrade the spectra. The apparatus can either be operated in the negative mode whereby negatively charged ions are detected, or in the positive mode whereby positively charged ions are detected. It is also possible that the apparatus could be arranged for simultaneous detection of positive and negative ions. This invention produces particular improvement to results when the apparatus is operated in the negative mode.

Ideally the gas contains air, and it may also comprise a sample of chemical vapour such as vapour from one or more of the following chemical warfare agents, explosives, narcotics or atmospheric pollutants and the like.

In another preferred embodiment, an ion mobility spectrometer comprises the apparatus for ionisation of a gas that is described above. The spectral results achieved from such a machine can be enhanced if Fourier transform techniques are applied to such an ion mobility spectrometer. This has the potential to enhance both the sensitivity and resolution of the signal compared to that achieved by a standard instrument.

The invention will now be described by reference to the following drawings in which;

FIG. 1 shows a typical prior art ion mobility spectrometer which employs a radioactive ionisation source;

FIG. 2 shows an ion mobility spectrometer which employs a continuous corona ionisation source;

FIG. 3 shows a device according to the present invention; and

Figure 4B:
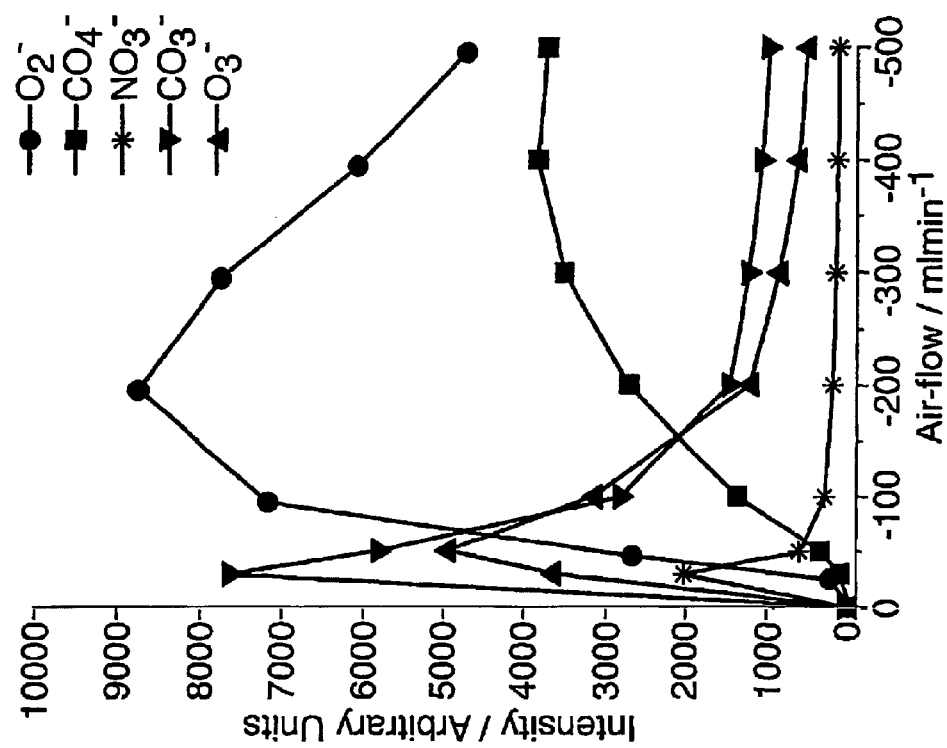
FIG. 4 shows experimental data related to ion production from a) the device described with reference to FIG. 2 and b) a device according to the present invention.

Referring to FIG. 1, an Ion Mobility Spectrometer 2 of the prior art comprises an ionisation region 4, a reaction region 6 and a drift region 8. These regions are bounded by metallic cylindrical walls 9, and a plurality of electrodes 11 are situated along the length of the reaction region 6 and the drift region 8. An electrical ion shutter 18, which typically comprises two thin wire grids to which voltages are applied, is situated between the reaction region 6 and the drift region 8.

A sample gas 10 is directed onto an inlet membrane 12. The inlet membrane 12 usually comprises a thin silicone rubber film and is used to remove water from the sample gas 10. Removal of water from the sample gas 10 using the inlet membrane 12 is not essential, but it is done because the presence of water tends to complicate the mobility spectra which are obtained.

Sample gas that has passed through the inlet membrane 12 combines with gas 14 which is flowing into the ionisation region 4 thereby producing a gas mixture 15 which passes into the ionisation region 4.

The ionisation region 4 contains a radioactive source 16, which is typically a beta radiation emitter such as $^{63}Ni$ foil. The radiation emitted by the radioactive source 16 causes ionisation of the gas mixture 15. After ionisation of the gas mixture 15 in the ionisation region 4, the gas flows into the reaction region 6 where various further chemical reactions may occur.

A uniform electric field is applied along the length of the reaction region 6 and the drift region 8 by application of appropriate voltages to the electrodes 11. Typically a uniform electric field of approximately 200 V/cm is used. Periodically, the shutter 18 is opened and ions 22 are injected into the drift region 8 under the influence of the electric field. Due to the flow rate of the drift gas 24, unionised portions of the gas mixture 15 tend not to enter the drift region 8.

Under the influence of the electric field and collisions with a counter-flowing drift gas 24, the ions 22 are injected into the drift region 8 and attain a constant velocity. Ions of low molecular weight will generally travel with a higher velocity than large ions of high molecular weight so that separation of the ions occurs within the drift region with the most mobile ions arriving at the collector 20 first. However, whilst mass plays a major part in the arrival time other parameters such as volume, shape and polarizability also play a role. The mobility spectrum obtained is characteristic of the ionised and reacted gas mixture 15.

The uniform electric field may be such that either negative or positive ions reach the collector. Using an electric field that results in the detection of negative ions at the collector 20 is termed negative mode operation, whilst the use of an electric field that results in the collection of positive ions is termed positive mode operation.

Typically both the gas 14 flowing through the ionisation and reaction regions, and the counter flowing drift gas 24 are air. In IMS devices containing a $^{63}$Ni ionisation source, $O_2^-$ and $CO_4^-$ are the principal ions that are produced when air is ionised. In the absence of any further chemical reactions, these $O_2^-$ and $CO_4^-$ ions provide the main contribution to the reactant ion peak (RIP) when operating in negative mode.

If the gas mixture 15 comprises air and a sample material (such as a chemical warfare agent, narcotics or explosives vapour), ionisation of air in the ionisation region 4 will produce $O_2^-$ and $CO_4^-$ ions. Generally, the sample material itself is not directly ionised by the radioactive source 16. Once the $O_2^-$ and $CO_4^-$ ions have been produced by the ionisation of air, they may chemically react with the sample material to produce ions that are characteristic of that sample material. The majority of the further chemical reactions occur in the reaction region 6.

Referring to the system of FIG. 2, a continuous corona ionisation source 26 has been used to replace the radioactive source 16 described with reference to FIG. 1. Continuous corona discharge sources are relatively inexpensive and simple and can also operate continuously consuming little power. However, despite much research, continuous corona discharge ionisation has not met the criteria required to replace radioactive ionisation sources. In particular, the ionic mobility spectra obtained using continuous corona discharge in an IMS system operating in negative mode has been found to be considerably different from that obtained using $^{63}$Ni ionisation source, and loss of sensitivity for detection of chemical warfare agents in this mode has been observed.

It is thought that the formation of neutral species such as ozone and $NO_x$ in the corona source is responsible for different negative-ion chemistry to that obtained with a $^{63}$Ni source. As described above, ionisation of air using a $^{63}$Ni source primarily causes the formation $O_2^-$ and $CO_4^-$ ions. In IMS devices of the type shown in FIG. 2, it is likely that neutral species (e.g. $O_3$, NO and $NO_2$) are formed in the corona (see, for example, B Gravendee and F J de Hoog, J Phys B: At Mol Phys 20, 6337 (1987)) and react with the $O_2^-$ and $CO_4^-$ ions, to produce further ions, via reactions such as:

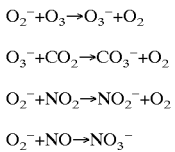

$$O_2^- + O_3 \rightarrow O_3^- + O_2$$

$$O_3^- + CO_2 \rightarrow CO_3^- + O_2$$

$$O_2^- + NO_2 \rightarrow NO_2^- + O_2$$

$$O_2^- + NO \rightarrow NO_3^-$$

The further ions (e.g. $O_3^-$, $CO_3^-$ and $NO_3^-$) produced by the reaction of the $O_2^-$ and $CO_4^-$ ions with the neutral species produced by the corona source are formed at the expense of the $O_2^-$ and $CO_4^-$ ions reacting with the sample material. These further ions tend not to react with sample material.

The effect of the neutral species on the negative ion chemistry is considered to be why continuous corona IMS systems of the type shown in FIG. 2 have been found to be ineffective when operated in negative mode.

Referring to FIG. 3, an IMS according to the present invention comprises an ionisation region 4, a reaction region 6 and a drift region 8. These regions are bounded by metallic cylindrical walls 9, and a plurality of electrodes 11 are situated along the length of the reaction region 6 and the drift region 8. An electrical ion shutter 18, which typically comprises two thin wire grids to which voltages are applied, is situated between the reaction region 6 and the drift region 8.

The ionisation region 4 contains a continuous corona ionisation source 26, which comprises a continuous corona needle to which a high voltage is applied (voltage source not shown). A plurality of commercially available continuous corona ionisation sources are known, and readily available, to those skilled in the art. In place of a continuous corona ionisation source, a person skilled in the art would recognise that non-continuous corona discharge sources (such as pulsed corona discharge sources) could also be employed.

Gas 10 that contains sample material (e.g. chemical warfare agent, explosive or narcotic vapours) is passed against an inlet membrane 12. The inlet membrane 12 permits a gas sample 13 to enter the reaction region 6.

Flush gas 32 combines with the gas sample 13 and passes through the reaction region 6 and past the continuous corona source 26 that is located in the ionisation region 4. Ions produced by the continuous corona ionisation source 26 are then moved through the reaction region 6 and toward the shutter 18 by the uniform electric field that is produced by the electrodes 11. Neutral species produced by the continuous corona ionisation source 26 are carried away from the ionisation region 4 by the flow of flush gas 32 that is in the opposite direction to the ions moving toward the shutter 18 under the influence of the electric field.

The removal of the neutral corona species from the site of their production before they can react with the corona-produced ions produces a collection of ions comparable to those produced by a radioactive ionisation source. Consequently, the ions produced in the reaction region 6 of the present invention by chemical reactions between the corona produced ions and the sample material are comparable to those produced in the reaction region of the system described with reference to FIG. 1.

To inject ions in to the drift region for ion analysis, the shutter 18 is periodically opened. Drift gas 24 flows through the drift region 8 and an ion mobility spectra, which is characteristic of the gas sample 13, is thus obtained.

The nature of the sample which is being detected will determine the temperature and pressure at which an IMS device according to this invention will be operated. For example, if vesicants are being detected the IMS will generally operate at ambient temperature and pressure. If narcotic or explosive vapour is being detected the IMS may be operated at an elevated temperature (possibly several hundred degrees Celsius) due to the involatile nature of the sample vapour. The optimum temperature and pressure of IMS operation when detecting different sample vapours would be well known to a person skilled in the art.

It is also immediately apparent to a person skilled in the art that sample material (e.g. vesicants, explosive or narcotic vapours) could be introduced into the reaction region 6 in a number of ways other than that described above. For example, the sample material could, possibly after being filtered by an appropriate inlet membrane, be mixed with the gas 32 prior to that gas entering the reaction region 6.

The essence of the present invention is attaining neutral species removal from a corona ionisation source by directing a gas flow in a different direction to the flow of ions from the corona, thereby effectively 'flushing' unwanted neutral species away from the region where subsequent chemical reactions take place. Numerous physical arrangements that could achieve this effect would be immediately apparent to those skilled in the art, and the particular system described with reference to FIG. 3 should in no way be seen as limiting the scope of the present invention.

Similarly, a person skilled in the art would recognise that the present invention is not only applicable to IMS devices (including Fourier transform IMS and ion trap IMS devices) but also to any apparatus in which chemical ionisation is performed. Examples of alternative applications of this invention include use in atmospheric pressure chemical ionisation mass spectrometry, or in the removal of unwanted ozone in electrostatic precipitators.

The advantages of the present invention are demonstrated by the experimental data given in FIG. 4.

Figure 4A:
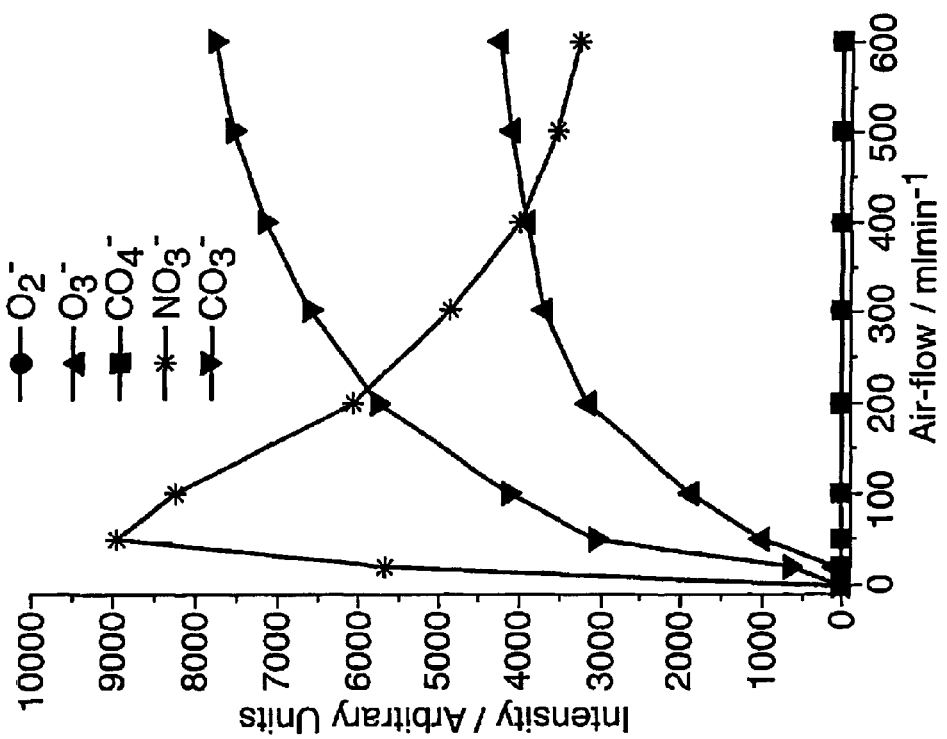

FIG. 4a shows the ionic species reaching the collector 20, in the absence of any sample material in the sample gas 10, as air is passed through a continuous corona IMS system of the type that is described above with reference to FIG. 2. It can be seen that the reactant ions $O_2^-$ and $CO_4^-$ that are produced when air is ionised by a $^{63}$Ni radioactive source are almost completely suppressed in this system. Less reactive ions such as $NO_3^-$, $CO_3^-$ and $O_3^-$ dominate over the range of flow rates used.

FIG. 4b shows the ionic species reaching the collector 20, in the absence of any sample material in the sample gas 10, as air is passed through a reverse flow continuous corona IMS system according to the present invention. Ions formed in the corona discharge are still directed towards the collector 20 under the influence of the electric field but neutral species no longer react with the corona-produced ions because they are removed from the reaction region 6 by the gas flow 32. This results in the reactant ions $O_2^-$ and $CO_4^-$ dominating, with the contribution of $NO_3^-$, $CO_3^-$ and $O_3^-$ reduced significantly, especially at higher flow rates.

Figure 5:
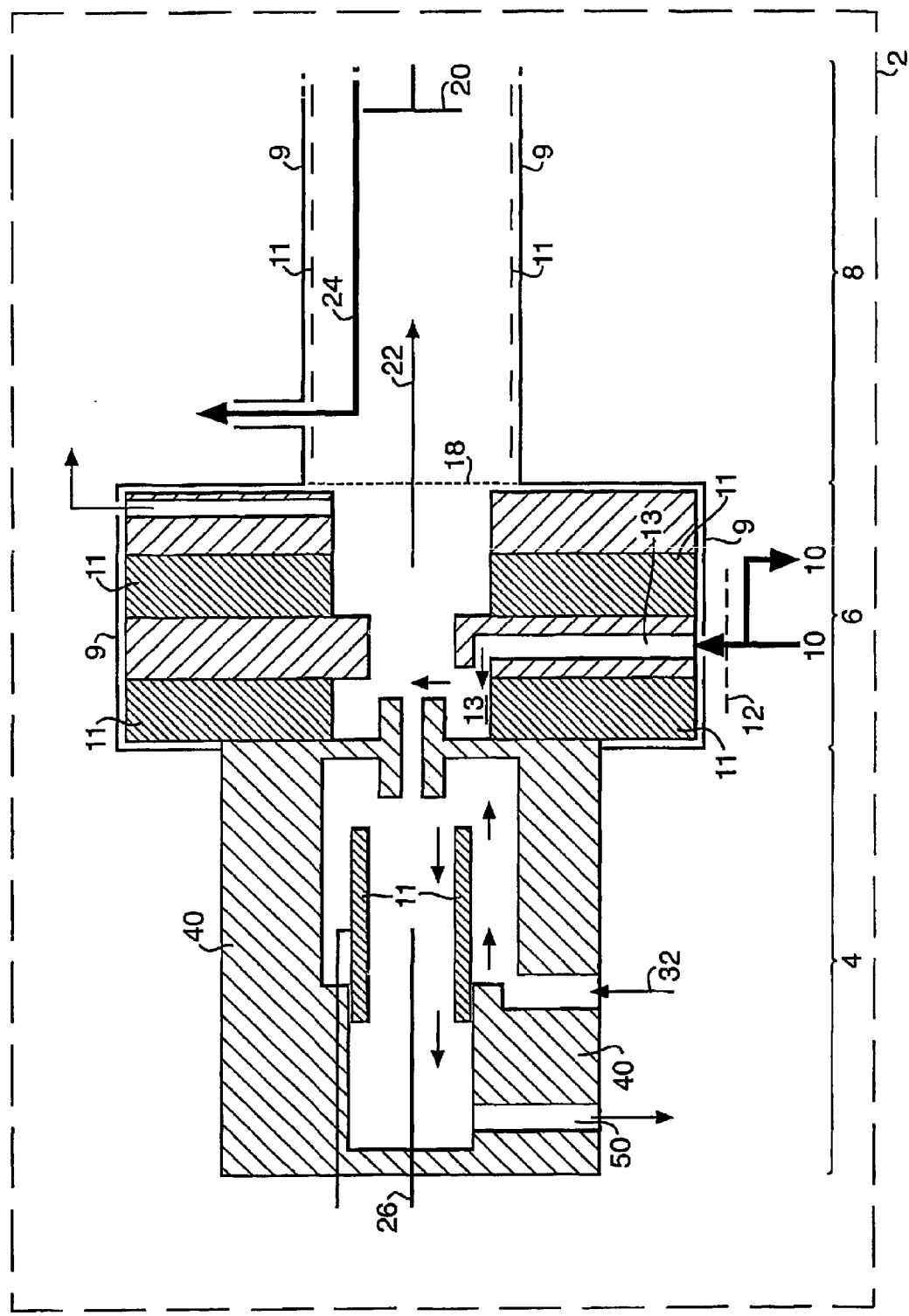
FIG. 5 shows an apparatus for ionisation of a gas comprising an ionisation region comprising a corona ionisation source, a reaction region and a drift region, wherein the means for flowing gas past the corona ionisation source has a flush inlet in the ionisation region and a flush outlet also in the ionisation region, and wherein the sample is introduced into the reaction region.

Referring to FIG. 5, an IMS according to the present invention comprises an ionisation region 4, a reaction region 6, and a drift region 8. The ionisation region 4 is bounded by PTFE walls 40. The reaction region 6 and the drift region 8 are bounded by metallic cylindrical walls 9. A plurality of electrodes 11 are situated along the length of the ionisation region, the reaction region and the drift region. An electrical ion shutter 18, which typically comprises two thin wire grids to which voltages are applied, is situated between the reaction region 6 and the drift region 8.

The ionisation region contains a continuous corona ionisation source 26, which comprises a continuous corona needle to which a high voltage is applied (voltage source not shown). Flush gas 32 enters the ionisation region and passes through the ionisation region towards the corona ionisation source 26. Once flush gas 32 has been ionised, the electrodes 11 move the charged species towards the reaction region 6. The flow of flush gas 32 through the ionisation region in substantially the opposite direction to the direction of flow of the charged species means that neutral species produced by the action of continuous corona ionisation source 26 on the flush gas 32 are carried away from ionisation region 4 and are exhausted through 50. These neutral species do not therefore enter the reaction region 6.

The sample gas 10 enters the reaction region 6 through an inlet membrane 12. This allows gas 13 to enter the reaction region. The reactant ion species, formed from flush gas 32, then interact with gas 13 to produce the ionised sample material 22. The ionised sample material 22 is moved towards the drift region by a series of electrodes 11. The shutter 18 is periodically opened to allow the ionised sample material 22 to enter the drift region 8. Once in the drift region 8, further electrodes 11 propel the ionised sample material 22 to the collector 20. Under the influence of the electric field produced by electrodes 11 and inert drift gas 24, travelling through the drift region in the opposite direction to the ionised sample material 22, the ions in the ionised sample material 22 separate. The most mobile ions in the reaction gas reach the collector 20 first.

Figure 6:
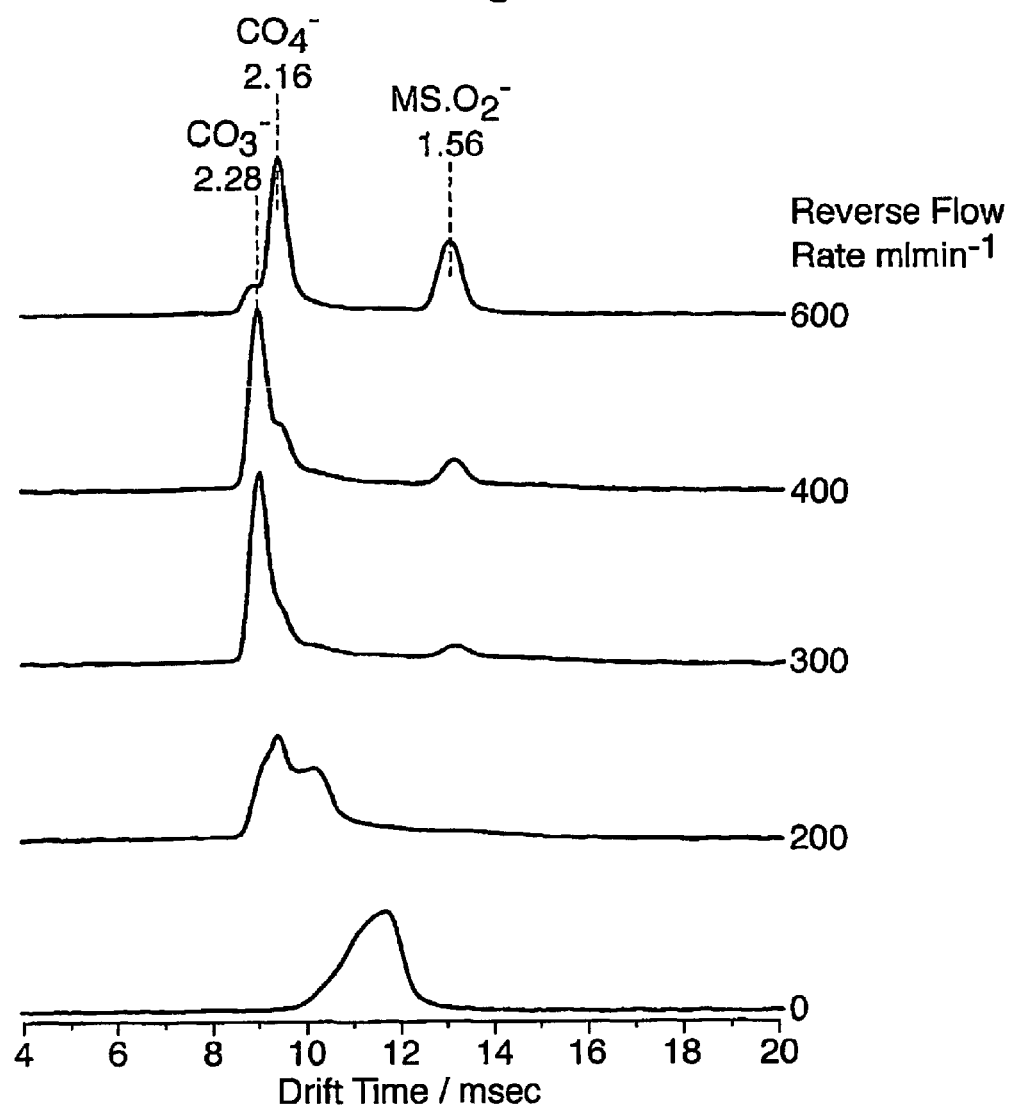
FIG. 6 shows an ion mobility spectrometer response in negative ion mode to methyl salicylate at different reverse flow rates.

Referring to FIG. 6 the data presented demonstrates the improved results that are obtained by use of the reverse gas flow. It also demonstrates that these results are continuously improved as the rate of reverse gas flow is increased within the limits of the rates that were used in this experiment. The experiments were conducted with the apparatus using a high corona energy of 10 $\mu$A operating in the reverse ion flow mode using methyl salicylate as the sample agent. This produces an adduct product ion $MS.O_2^-$ at a reduced mobility ($K_0$) of 1.56 $cm^2V^{-1}s^{-1}$. The results show that the nature of the reactant ion peak changes significantly as the gas flow past the corona needle is reduced. When a flow rate in the region of 600 mlmin$^{-1}$ the dominant peak at 2.16 $cm^2V^{-1}s^{-1}$ was identified as representing the $O_2^-$ and $CO_2.O_2^-$ ion and the smaller peak at 2.28 $cm^2V^{-1}s^{-1}$ was identified as representing the $CO_3^-$ ion series. At this high flow rate the reactant ion peak region is very similar to that seen when using a traditional $^{63}$Ni radioactive ionisation source (not shown). As the flow past the needle is reduced, so the shape and position of the reactant ion peak changes. When the flow rate is in the region of 300-500 mlmin$^{-1}$ there is a reduction in the level of $O_2^-$ and $CO_2.O_2^-$ ions that are identified and an increase in the level of $CO_3^-$ ion series peak. As the reverse flow rate continues to decrease the reactant ion peak at the higher mobility values reduces and a new broad peak at a lower value is seen to develop. This peak has been identified as being associated with oxides of nitrogen such as $NO_3^-$, $NO_2^-$, $NO_3.HNO_3^-$ and the like. In addition as the flow rate decreases the methyl salicylate adduct ion peak reduces. It is believed that the sharp product ion peak observed at the high flow rates is a result of the rapid flushing away of the high concentration of ozone and $NO_x$ formed in the ionisation region. As the flow rate is reduced the ozone and $NO_x$ is not removed as effectively. The result is that the ozone and $NO_x$ is able to interact with the $O_2^-$ and $CO_2.O_2^-$ ions initially generated meaning that the $MS.O_2^-$ adduct ion is not able to be as readily formed. This results in a significant degrading of the quality of the spectra obtained, as demonstrated in FIG. 6 where at a flow rate of 200 mlmin$^{-1}$ there is no evidence of the product adduct ion.

The ion profiles produced by the present invention, when air is ionised, are very similar to those observed with a $^{63}$Ni radioactive source. Although air has been described in this example, the present invention is also applicable when other gases (e.g. nitrogen, oxygen, carbon dioxide etc) are used. Although the focus of this work has been negative ion chemistry it is also believed that this technique could provide advantages when using a corona ionisation source for positive ion chemistry. In these systems there is evidence that the ozone and $NO_x$ produced during the ionisation phase may react with unsaturated and aromatic compounds in the sample material with the result that a degradation in the spectra is observed. It is believed that by using a reverse gas flow corona ionisation apparatus such as the one disclosed herein such unwanted reactions may be reduced or eliminated.

The present invention thus provides an IMS system that can operate in either positive or negative mode, using a non-radioactive corona ionisation source, and provides performance comparable to IMS systems incorporating radioactive ionisation sources.

What is claimed is:

1. Apparatus for ionization of a gas comprising:
   (a) an ionization region, a reaction region and a drift region;
   (b) a shutter grid which separates the reaction region from the drift region;
   (c) a corona ionization source;
   (d) means for flowing a first gas past the corona ionization source, wherein the first gas is exhausted from the apparatus in the ionization region;
   (e) means for applying an electric field to move any ions produced by the corona ionization source away from the corona ionization source;
   (f) means for flowing a second gas through the drift region, wherein the direction of the first gas flow past the corona ionization source is substantially different to the direction of flow of the ions in the electric field and wherein the second gas is exhausted from the apparatus in the drift region.

2. Apparatus for ionization of a gas as claimed in claim 1 wherein the corona ionization source is a continuous corona ionization source.

3. Apparatus for ionization of a gas as claimed in claim 1 wherein the flow of a first gas past the corona ionization source is continuous.

4. Apparatus for ionization of a gas as claimed in claim 1 wherein the flow of a first gas past the corona ionization source occurs periodically.

5. Apparatus for ionization of a gas as claimed in claim 1 wherein the first gas flowing past the corona ionization source is air.

6. Apparatus for ionization of a gas as claimed in claim 5 wherein the first gas additionally comprises a vesicant.

7. Apparatus for ionization of a gas as claimed in claim 5 wherein the first gas additionally comprises explosives vapour.

8. Apparatus for ionization of a gas as claimed in claim 5 wherein the first gas additionally comprises narcotics vapour.

9. Apparatus for ionization of a gas as claimed in claim 1 wherein the flow rate of the means for flowing a first gas past the corona ionization source is adjustable.

10. Apparatus for ionization of a gas as claimed in claim 1 wherein the sample material is introduced into the reaction region.

11. Apparatus for ionization of a gas as claimed in claim 1 wherein the flow rate of the means for flowing a second gas through the drift region is adjustable.

12. Apparatus for ionization of a gas as claimed in claim 11 wherein the flow rate of the means for flowing a first gas past the corona ionization source is independently adjustable from the flow rate of the means for flowing a second gas through the drift region.

13. Apparatus for ionization of a gas as claimed in claim 1 wherein the ions are negatively charged.

14. Apparatus for ionization of a gas as claimed in claim 1 wherein the ions are positively charged.

15. Apparatus for ionization of a gas as claimed in claim 1 wherein the flow of a first gas past the corona ionization source has a flush inlet in the ionization region and a flush outlet also in the ionization region.

16. An ion mobility spectrometer comprising the apparatus for ionization of a gas as claimed in claim 1.

17. Apparatus for ionization of a gas as claimed in claim 1 in which the ionization region and the reaction region are, at least in part, separately bounded.

18. Apparatus for ionization of a gas as claimed in claim 17 in which PTFE walls bound the ionization region and metallic cylindrical walls bound the reaction region.

19. Apparatus for ionization of a gas as claimed in claim 17 in which a boundary for the ionization region comprises a wall having an outlet through which the first gas is exhausted.

* * * * *